United States Patent
Haddad et al.

(10) Patent No.: US 8,442,841 B2
(45) Date of Patent: May 14, 2013

(54) PATIENT SELECTION METHOD FOR ASSISTING WEIGHT LOSS

(75) Inventors: Walid Haddad, Closter, NJ (US); Shai Policker, Tenafly, NJ (US); Keren Afek, Haifa (IL)

(73) Assignee: Matacure N.V., Curacao (AN)

( * ) Notice: Subject to any disclaimer, the term of this patent is extended or adjusted under 35 U.S.C. 154(b) by 951 days.

(21) Appl. No.: 11/551,282

(22) Filed: Oct. 20, 2006

(65) Prior Publication Data

US 2007/0092446 A1      Apr. 26, 2007

Related U.S. Application Data

(60) Provisional application No. 60/728,658, filed on Oct. 20, 2005.

(51) Int. Cl.
*G06Q 10/00* (2006.01)
*G06Q 50/00* (2006.01)

(52) U.S. Cl.
USPC .............................................................. 705/2

(58) Field of Classification Search ................ 705/2, 3
See application file for complete search history.

(56) References Cited

U.S. PATENT DOCUMENTS

| | | |
|---|---|---|
| 3,411,507 A | 11/1968 | Wingrove |
| 3,516,412 A | 6/1970 | Ackerman |
| 3,737,579 A | 6/1973 | Bolduc |
| 4,000,745 A | 1/1977 | Goldberg et al. |
| 4,010,758 A | 3/1977 | Rockland et al. |
| 4,133,315 A | 1/1979 | Berman et al. |
| 4,177,818 A | 12/1979 | De Pedro |
| 4,235,246 A | 11/1980 | Weiss |
| 4,280,503 A | 7/1981 | Ackerman |
| 4,313,448 A | 2/1982 | Stokes |
| 4,357,946 A | 11/1982 | Dutcher et al. |
| 4,378,023 A | 3/1983 | Trabucco |
| 4,416,267 A | 11/1983 | Garren et al. |
| 4,452,254 A | 6/1984 | Goldberg et al. |
| 4,485,805 A | 12/1984 | Foster, Jr. |
| 4,592,339 A | 6/1986 | Kuzmak |

(Continued)

FOREIGN PATENT DOCUMENTS

| | | |
|---|---|---|
| EP | 0057048 | 8/1982 |
| EP | 0129483 | 12/1984 |

(Continued)

OTHER PUBLICATIONS

J.D.Z. Chen et al., "Detection of gastric slow wave propagation from the cutaneous electrogastrogram", Am. J. Physiol. vol. 277 1999 p. G424-G430.*

(Continued)

*Primary Examiner* — Gerald J. O'Connor
*Assistant Examiner* — Trang Nguyen
(74) *Attorney, Agent, or Firm* — William H. Dippert; Eckert Seamans Cherin & Mellot, LLC

(57) ABSTRACT

A method is provided for identifying a patient as being suitable for implantation of a weight-loss assist device. The method includes identifying the patient as being generally suitable for the implantation and subsequently, measuring a value associated with the patient. Responsively to determining that the value is beyond a threshold associated therewith, the weight-loss assist device is implanted.

35 Claims, 6 Drawing Sheets

U.S. PATENT DOCUMENTS

| | | | |
|---|---|---|---|
| 4,823,808 A | 4/1989 | Clegg et al. | |
| 4,975,682 A | 12/1990 | Kerr et al. | |
| 5,074,868 A | 12/1991 | Kuzmak | |
| 5,101,814 A | 4/1992 | Palti | |
| 5,103,804 A | 4/1992 | Abele | |
| 5,105,812 A | 4/1992 | Corman | |
| 5,188,104 A | 2/1993 | Wernicke et al. | |
| 5,190,041 A | 3/1993 | Palti | |
| 5,226,429 A | 7/1993 | Kuzmak | |
| 5,234,454 A | 8/1993 | Bangs | |
| 5,247,938 A | 9/1993 | Silverstein et al. | |
| 5,263,480 A | 11/1993 | Wernicke et al. | |
| 5,301,105 A * | 4/1994 | Cummings, Jr. | 705/2 |
| 5,314,463 A | 5/1994 | Camps et al. | |
| 5,368,028 A | 11/1994 | Palti | |
| 5,423,872 A | 6/1995 | Cigaina | |
| 5,449,368 A | 9/1995 | Kuzmak | |
| 5,514,175 A | 5/1996 | Kim et al. | |
| 5,540,730 A | 7/1996 | Terry et al. | |
| 5,551,425 A | 9/1996 | Essen-Moller | |
| 5,601,604 A | 2/1997 | Vincent | |
| 5,690,691 A | 11/1997 | Chen et al. | |
| 5,704,368 A | 1/1998 | Asano et al. | |
| 5,716,385 A | 2/1998 | Mittal et al. | |
| 5,741,211 A | 4/1998 | Renirie et al. | |
| 5,792,210 A | 8/1998 | Wamubu et al. | |
| 5,795,304 A | 8/1998 | Sun et al. | |
| 5,836,994 A | 11/1998 | Bourgeois | |
| 5,837,006 A | 11/1998 | Ocel et al. | |
| 5,861,014 A | 1/1999 | Familoni | |
| 5,868,141 A | 2/1999 | Ellias | |
| 5,919,216 A | 7/1999 | Houben et al. | |
| 5,938,669 A | 8/1999 | Klaiber et al. | |
| 5,979,449 A | 11/1999 | Steer | |
| 5,991,649 A | 11/1999 | Garfield et al. | |
| 5,995,872 A | 11/1999 | Bourgeois | |
| 6,026,326 A | 2/2000 | Bardy | |
| 6,041,258 A | 3/2000 | Cigaina et al. | |
| 6,067,991 A | 5/2000 | Forsell | |
| 6,083,249 A | 7/2000 | Familoni | |
| 6,091,992 A | 7/2000 | Bourgeois | |
| 6,092,528 A | 7/2000 | Edwards | |
| 6,093,167 A | 7/2000 | Houben et al. | |
| 6,104,955 A | 8/2000 | Bourgeois | |
| 6,115,635 A | 9/2000 | Bourgeois | |
| 6,129,685 A | 10/2000 | Howard | |
| 6,132,372 A | 10/2000 | Essen-Moller | |
| 6,135,978 A | 10/2000 | Houben | |
| 6,216,045 B1 | 4/2001 | Black et al. | |
| 6,243,607 B1 | 6/2001 | Mintchev | |
| 6,249,697 B1 | 6/2001 | Asano et al. | |
| 6,261,280 B1 | 7/2001 | Houben et al. | |
| 6,334,073 B1 | 12/2001 | Levine | |
| 6,363,937 B1 | 4/2002 | Hovda | |
| 6,368,284 B1 * | 4/2002 | Bardy | 600/508 |
| 6,381,495 B1 | 4/2002 | Jenkins | |
| 6,405,732 B1 | 6/2002 | Edwards | |
| 6,411,842 B1 | 6/2002 | Cigaina et al. | |
| 6,415,178 B1 | 7/2002 | Ben-Haim et al. | |
| 6,427,089 B1 | 7/2002 | Knowlton | |
| 6,449,511 B1 | 9/2002 | Mintchev | |
| 6,454,699 B1 | 9/2002 | Forsell | |
| 6,535,764 B2 | 3/2003 | Imran | |
| 6,571,127 B1 | 5/2003 | Ben-Haim et al. | |
| 6,572,542 B1 | 6/2003 | Houben et al. | |
| 6,584,348 B2 | 6/2003 | Glukhovsky | |
| 6,591,137 B1 | 7/2003 | Fischell et al. | |
| 6,600,953 B2 | 7/2003 | Flesler et al. | |
| 6,606,523 B1 | 8/2003 | Jenkins | |
| 6,609,025 B2 | 8/2003 | Barrett et al. | |
| 6,612,983 B1 | 9/2003 | Marchal | |
| 6,652,444 B1 | 11/2003 | Ross | |
| 6,658,297 B2 | 12/2003 | Loeb | |
| 6,684,104 B2 | 1/2004 | Gordon | |
| 6,735,477 B2 | 5/2004 | Levine | |
| 6,745,079 B2 | 6/2004 | King | |
| 6,754,536 B2 | 6/2004 | Swoyer | |
| 6,826,428 B1 | 11/2004 | Chen | |
| 6,832,114 B1 | 12/2004 | Whitehurst | |
| 6,852,110 B2 | 2/2005 | Roy et al. | |
| 6,853,862 B1 | 2/2005 | Marchal et al. | |
| 6,869,431 B2 | 3/2005 | Maguire | |
| 6,876,885 B2 | 4/2005 | Swoyer | |
| 6,895,279 B2 | 5/2005 | Loeb et al. | |
| 6,918,906 B2 | 7/2005 | Long | |
| 6,939,349 B2 | 9/2005 | Fleischman | |
| 6,947,792 B2 | 9/2005 | Ben-Haim | |
| 6,952,613 B2 | 10/2005 | Swoyer et al. | |
| 7,006,871 B1 | 2/2006 | Darvish et al. | |
| 7,043,295 B2 | 5/2006 | Starkebaum | |
| 7,054,690 B2 | 5/2006 | Imran | |
| 7,067,498 B2 * | 6/2006 | Wolf et al. | 514/54 |
| 7,076,305 B2 | 7/2006 | Imran et al. | |
| 7,076,306 B2 | 7/2006 | Marchal et al. | |
| 2001/0011543 A1 | 8/2001 | Forsell | |
| 2002/0026141 A1 | 2/2002 | Houben | |
| 2002/0103424 A1 | 8/2002 | Swoyer et al. | |
| 2002/0161414 A1 | 10/2002 | Flesler et al. | |
| 2003/0045919 A1 | 3/2003 | Swoyer | |
| 2003/0055464 A1 | 3/2003 | Darvish et al. | |
| 2003/0055467 A1 | 3/2003 | Ben-Haim et al. | |
| 2003/0066536 A1 | 4/2003 | Forsell | |
| 2003/0144708 A1 | 7/2003 | Starkebaum | |
| 2003/0195600 A1 | 10/2003 | Tronnes et al. | |
| 2003/0208212 A1 | 11/2003 | Cigaina | |
| 2003/0208242 A1 | 11/2003 | Harel et al. | |
| 2003/0220678 A1 | 11/2003 | Tronnes | |
| 2004/0044376 A1 | 3/2004 | Flesler et al. | |
| 2004/0059393 A1 * | 3/2004 | Policker et al. | 607/40 |
| 2004/0088023 A1 | 5/2004 | Imran | |
| 2004/0107004 A1 | 6/2004 | Levine et al. | |
| 2004/0147816 A1 | 7/2004 | Policker et al. | |
| 2004/0158138 A1 | 8/2004 | Kilcoyne | |
| 2004/0162469 A1 | 8/2004 | Imran | |
| 2004/0162595 A1 | 8/2004 | Foley | |
| 2004/0167583 A1 | 8/2004 | Knudson et al. | |
| 2004/0193184 A1 | 9/2004 | Laufer | |
| 2004/0236316 A1 | 11/2004 | Danitz | |
| 2004/0249421 A1 | 12/2004 | Harel et al. | |
| 2005/0020965 A1 | 1/2005 | Rioux | |
| 2005/0021101 A1 * | 1/2005 | Chen et al. | 607/40 |
| 2005/0055038 A1 | 3/2005 | Kelleher et al. | |
| 2005/0065505 A1 | 3/2005 | Ryan | |
| 2005/0075654 A1 | 4/2005 | Kelleher | |
| 2005/0080462 A1 * | 4/2005 | Jenkins et al. | 607/58 |
| 2005/0090873 A1 | 4/2005 | Imran | |
| 2005/0107829 A1 | 5/2005 | Edwards | |
| 2005/0143784 A1 | 6/2005 | Imran | |
| 2005/0164925 A1 | 7/2005 | Jakubowski et al. | |
| 2005/0183732 A1 | 8/2005 | Edwards | |
| 2005/0192615 A1 | 9/2005 | Torre et al. | |
| 2005/0203500 A1 | 9/2005 | Saadat | |
| 2005/0209653 A1 | 9/2005 | Herbert et al. | |
| 2005/0222638 A1 | 10/2005 | Foley et al. | |
| 2006/0074459 A1 | 4/2006 | Flesler et al. | |
| 2006/0085045 A1 | 4/2006 | Harel et al. | |
| 2006/0142803 A1 | 6/2006 | Mintchev | |
| 2006/0173238 A1 | 8/2006 | Starkebaum | |
| 2006/0184207 A1 | 8/2006 | Darvish et al. | |
| 2006/0247718 A1 | 11/2006 | Starkebaum | |
| 2007/0027493 A1 | 2/2007 | Ben-Haim et al. | |
| 2007/0051849 A1 | 3/2007 | Watts et al. | |
| 2007/0060812 A1 | 3/2007 | Harel et al. | |
| 2007/0060971 A1 | 3/2007 | Glasberg et al. | |
| 2007/0092446 A1 | 4/2007 | Haddad et al. | |
| 2007/0156177 A1 | 7/2007 | Harel et al. | |
| 2007/0179556 A1 | 8/2007 | Ben Haim et al. | |
| 2007/0185540 A1 | 8/2007 | Ben-Haim et al. | |
| 2007/0299320 A1 | 12/2007 | Policker et al. | |
| 2008/0046062 A1 | 2/2008 | Camps et al. | |
| 2008/0058889 A1 | 3/2008 | Ben-Haim et al. | |
| 2008/0058891 A1 | 3/2008 | Ben-Haim et al. | |
| 2008/0065168 A1 | 3/2008 | Bitton et al. | |
| 2008/0178684 A1 | 7/2008 | Spehr | |
| 2009/0062893 A1 | 3/2009 | Spehr | |
| 2009/0088816 A1 | 4/2009 | Harel et al. | |
| 2009/0118797 A1 * | 5/2009 | Kliger et al. | 607/62 |

| | | | |
|---|---|---|---|
| 2009/0131993 | A1 | 5/2009 | Rousso et al. |
| 2009/0204063 | A1 | 8/2009 | Policker et al. |
| 2009/0281449 | A1 | 11/2009 | Thrower et al. |
| 2010/0228105 | A1 | 9/2010 | Policker et al. |
| 2010/0305468 | A1 | 12/2010 | Policker et al. |
| 2010/0324644 | A1 | 12/2010 | Levi et al. |

FOREIGN PATENT DOCUMENTS

| | | |
|---|---|---|
| EP | 144705 | 3/1990 |
| EP | 1036545 | 9/2000 |
| EP | 1 447 052 | 8/2004 |
| JP | 2003/319945 | 11/2003 |
| JP | 2003319945 | 11/2003 |
| WO | WO 94/01172 | 1/1994 |
| WO | WO 97/25098 | 7/1997 |
| WO | WO 98/10830 | 3/1998 |
| WO | WO 99/03533 | 1/1999 |
| WO | WO 00/53257 | 9/2000 |
| WO | WO 01/10375 | 2/2001 |
| WO | WO 01/41671 | 6/2001 |
| WO | WO 01/66183 | 9/2001 |
| WO | WO 01/83019 | 11/2001 |
| WO | WO 01/91854 | 12/2001 |
| WO | WO 02/053093 | 7/2002 |
| WO | 02/082968 | 10/2002 |
| WO | WO 02/082968 | 10/2002 |
| WO | WO 02/089655 | 11/2002 |
| WO | WO 03/020365 | 3/2003 |
| WO | WO 03/045493 | 6/2003 |
| WO | WO 2004/021858 | 3/2004 |
| WO | WO 2004/043280 | 5/2004 |
| WO | 2004/066903 | 8/2004 |
| WO | WO 2004/069330 | 8/2004 |
| WO | 2004/091361 | 10/2004 |
| WO | WO 2004/096337 | 11/2004 |
| WO | WO 2004/112563 | 12/2004 |
| WO | WO 2004/112883 | 12/2004 |
| WO | 2005/007232 | 1/2005 |
| WO | WO 2005/007232 | 1/2005 |
| WO | WO 2005/007237 | 1/2005 |
| WO | 2005/009288 | 2/2005 |
| WO | WO 2005/016181 | 2/2005 |
| WO | WO 2005/023081 | 3/2005 |
| WO | 2005/037152 | 4/2005 |
| WO | WO 2005/037152 | 4/2005 |
| WO | WO 2005/041749 | 5/2005 |
| WO | 2005/087310 | 9/2005 |
| WO | WO 2005/087310 | 9/2005 |
| WO | WO 2006/018851 | 2/2006 |
| WO | WO 2006/035446 | 4/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2006/118790 | 11/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

Jaremko, et al., "Advances toward the implantable artificial pancreas for treatment of diabetes", Diabetes Care, 21(3), Mar. 1998.

Lamb F.S. et al., "Cyclosporine augments reactivity of isolated blood vessels", Life Sciences, 40, pp. 2571-2578, 1987.

Johansson B. et al., "Static and dynamic components in the vascular myogenic response to passive changes in length as revealed by electrical and mechanical recordings from the rat portal vein", Circulation Research, 36, pp. 76-83, 1975.

Zelcer E. et al., "Spontaneous electrical activity in pressurized small mesenteric arteries", Blood Vessels, 19, pp. 301-310, 1982.

Schobel. H.P. et al., "Preeclampsia—a state of sympathetic overactivity", New England Journal of Medicine, 335, pp. 148-1485, 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity. II. Mitochondrial variables", American Journal of Physiology, 274(4 Pt 1): C1174-1184, Apr. 1998.

Yamada, "Effects of drugs on electromechanical activities of the stomach and duodenum of conscious dogs", Nippon Heikatsukin Gakkai Zasshi. Feb. 1983;19(1):25-35. (abstract only).

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.

T Vilsboll and Associates, Research design and methods, Diabetes, vol. 50, Mar. 2001, pp. 610-613.

Jeannie F. Todd, et al, "Subcutaneous glucagons-like peptide-1 improves postprandial glycaemic control over 3-week period in patients with early type 2 diabetes", Clinical Science (1998) 95, 325-329.

Daniel J. Drucker, "Development of glucagon-like peptide-1-based pharmaceuticals as therapeutic agents for the treatment of diabetes", Current Pharmaceutical Design, 2001, 7, 1399-1412.

Shemerovskii KA, "Effect of feeding on the activity of duodenal smooth muscle in dogs", Biull Eksp Biol Med. Oct. 1978;86(10):394-7. (Abstract only).

U.S. Appl. No. 10/237,263.

Choi, et al—"[13C] Octanoic Acid Breath Test for Gastric Emptying of Solids . . . " Gastroenterology, 112, 1997, pp. 1155-1162.

English, et al—"Food Fails to Suppress Gherlin Levels in Obese Humans", J. Clin. Endocrinol. Metab., Jun. 2002 87(6) 2984-2987.

Tougas, et al—"Assessment of Gastric Emptying Using a Low Fat Meal: . . . ", American Journal of Gastroenterology, 95(6), pp. 1456-1462.

International Search Report and the Written Opinion Dated Sep. 2, 2011 From the International Searching Authority Re. Application No. PCT/IL 11/00116.

* cited by examiner

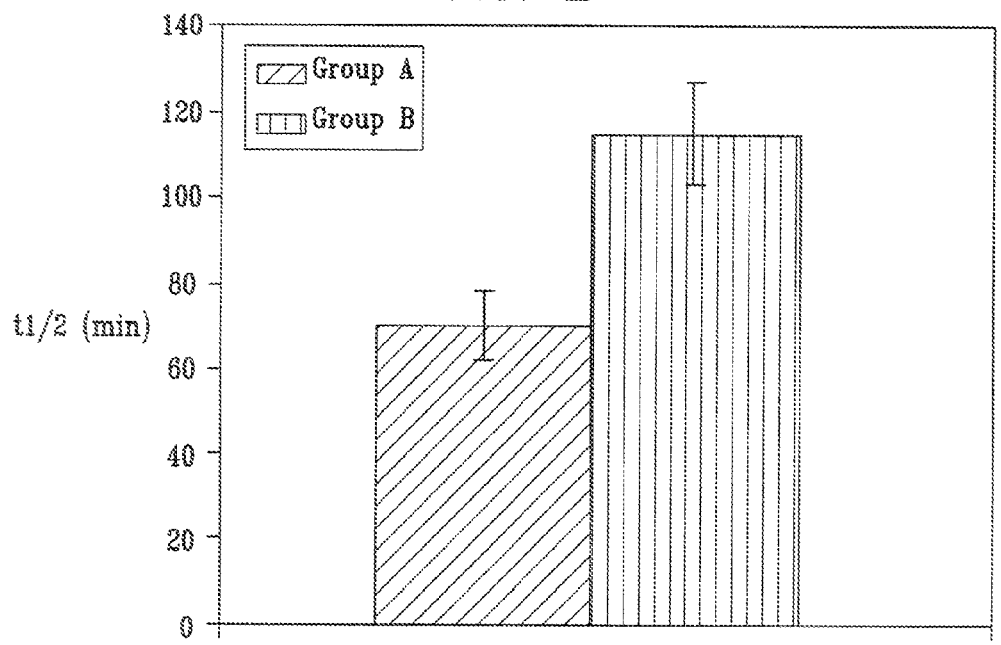
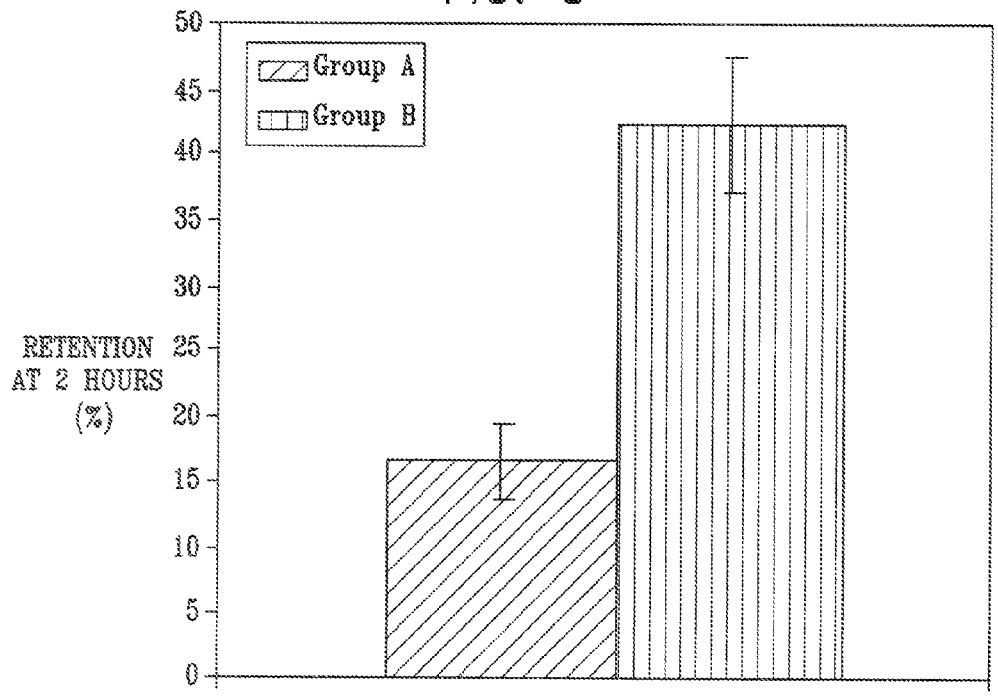

PATIENT SELECTION METHOD FOR ASSISTING WEIGHT LOSS

CROSS-REFERENCES TO RELATED APPLICATIONS

The present application claims the benefit of U.S. Provisional Patent Application 60/728,658 to Haddad et al., filed Oct. 20, 2005, entitled "Patient; selection method for obesity treatment." which is assigned to the assignee of the present patent application and is incorporated herein by reference.

FIELD OF THE INVENTION

The present invention relates generally to assisting weight loss, and specially to screening procedures for determining a patient's suitability for implantation of a weight-loss assist device.

BACKGROUND OF THE INVENTION

Obesity is a difficult to treat chronic condition defined by a body mass index (BMI=mass/height$^2$[kg/m]) greater than 30. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

U.S. Pat. No. 6,600,953 to Flesler et al., which is assigned to the assignee of the present patent application and is incorporated herein by reference, describes apparatus for treating a condition such as obesity. The apparatus includes a set of one or more electrodes, which are adapted to be applied to one or more respective sites in a vicinity of a body of a stomach of a patient. A control unit is adapted to drive the electrode set to apply to the body of the stomach a signal, configured such that application thereof increases a level of contraction of muscle tissue of the body of the stomach, and decreases a cross-sectional area of a portion of the body of the stomach for a substantially continuous period greater than about 3 seconds.

U.S. Pat. No. 6,571,127 and PCT Patent Publication WO 99/03533 to Ben-Haim et a., which are incorporated herein by reference, describe apparatus and methods for applying signals to smooth muscle so as to modify the behavior thereof. In particular, apparatus for controlling the stomach is described in which a controller applies an electrical field to, electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof without inducing action potentials in the cells, is referred to as Excitable-Tissue Control (ETC). Use of an ETC signal is described with respect to treating obesity, by applying the ETC signal to the stomach so as to delay or prevent emptying of the stomach. In addition, a method is described for increasing the motility of the gastrointestinal tract, by applying an ETC signal to a portion of the tact in order to increase the contraction force generated in the portion and the stretching of nearby tissue.

U.S. Patent Application Publication 2004/0147816 to Policker et al., which is assigned to the assignee of the present patent application and is incorporated herein by reference, describes diet evaluation gastric apparatus, which detects when a patient swallows, and detects the type and amount of matter ingested. The apparatus includes electrodes adapted to be coupled to the fundus and antrum of the patient and to measure electrical and mechanical activity therein, and a control unit to analyze such electrical and mechanical activity and optionally apply electrical energy to modify the activity of tissue of the patient.

In an article by Tougas et al., entitled, "Assessment of gastric emptying using a low fat meal: Establishment of international control values, " American Journal of Gastroenterology, 95(6), 2000, pp. 1456-1462, which is incorporated herein by reference, a study is described in which a simplified scintigraphic measurement of gastric emptying was compared to coventional gastric scintigraphic techniques and normal gastric emptying values defined in healthy subjects.

An article by Choli et at., entitled, "[$^{13}$C] Octanoic acid breath test for gastric emptying of solids: Accuracy, reproducibility, and comparison with scintigraphy," Gastroenterology, 112, 1997, pp. 1155-1162, which is incorporated herein by reference, describes a breath test using $^{13}$C to measure gastric emptying of solids.

An article by English et at., entitled, "Food fails to suppress ghrelin levels in obese humans, " J Clin Endocrinol Metab, June 2002, 87(6): 2984-2987, which is incorporated herein by reference, describes ghrelin as the first circulating hormone shown to stimulate feeding in humans following systemic administration. Food consumption was known to decrease circulating ghrelin concentrations in lean subjects. The authors investigated the effects of a test meal on plasma ghrelin and leptin cocentrations in 13 lean and 10 obese subjects. Fasting ghrelin was significantly higher in lean than in obese subjects, and fell by 39.5% thirty minutes after eating in the lean group before returning rapidly towards baseline values. There was no change in circulating, ghrelin in the obese group. Circulating leptin concentration also fell acutely 15 minutes following food intake in lean but not obese subjects. The authors concluded that (a) obese subjects do not exhibit the decline in plasma ghrelin and leptin seen after a meal in the lean, and (b) the role of the decline in leptin is unclear but given the orexigenic properties of ghrelin, the lack of suppression following a meal in obese subjects could lead to increased food consumption and suggests that ghrelin may be involved in the patlhophysiology of obesity.

SUMMARY OF THE INVENTION

In some embodiments of the present invention, a patient is identified who appears to be a generally-suitable candidate for implantation of a weight-loss assist device. For example, a generally-suitable candidate may be identified based on weight, height, age, and desire to undergo the implantation procedure. Subsequently, once the candidate has been identified as being generally suitable, one or more further tests are performed in order to determine whether the candidate is in: (a) a first population, which includes patients who are likely to benefit from the implantation of the device, or (b) a second population, which includes patients who are not likely to derive substantial. benefit from the implantation An example of a benefit derived from the device is defined by at least a threshold amount of weight loss following activation of the implanted device, compared to the patient's pre-implantation weight. In an embodiment, the threshold weight loss is a level of excess weight loss (EWL) of about 10% attained during a time period of about 6-20 weeks. Alternatively, benefit is defined using thresholds of EML equal to about 20%, 30%, or 40%. Alternatively, is additionally, a benefit derived from the device is expressed using a measure other than weight loss, such as, for example, improved control of blood sugar or another blood component, improved self-reported body image, or an improved cardiovascular parameter.

In accordance with an embodiment of the present invention, patients are determined to be in the first or second population based upon a rate of gastric emptying. Typically, if the rate of gastric emptying is faster than a threshold, ten the patient is determined to be likely to benefit from implantation of the device. For example, if the patient's gastric half-emptying time is less than about 80, 90, or 100 minutes, then the patient may be determined to be likely to benefit from implantation. Alternativey or additionally, if the level of gastric retention at two hours is less than about 20%, 30%, or 40%, then the patient may be determined to be likely to benefit from implantation.

In accordance with an embodiment of the present invention, a patient who is identified as being a generally-suitable candidate is placed into an evaluation program. During the evaluation program, the patient is weighed and counseled regarding changes in diet an/or lifestyle which are likely to help produce weight loss. Alternatively, the patient is not counseled, but is tracked during the evaluation period. At a later points (e.g., about 2-6 weeks o) about 6-20 weeks following counselling or initiation of tracking), the patient's weight is measured again. An excess weight loss greater than, for example, about 2%, 2.5%, 2.75%, or 3% is used to determine that the patient is likely to benefit from implantation.

In an embodiment, a weighted or non-weighted combination score is derived based on fast gastric emptying and weight loss during the evaluation period. For some applications the combination score allows patients whose gastric emptying rate is not sufficient to justify implantation to nevertheless have the device implanted if weight loss during the evaluation period is sufficiently high. Alternatively or additionally, the combination score allows patients whose weight loss during the evaluation period is not sufficient to justify implantation to nevertheless have the device implanted if the gastric emptying rate is sufficiently high.

In an embodiment, a patient is expected to have both a threshold gastric emptying rate and a threshold weight loss during the evaluation period in order to be determined to be likely to benefit from implantation.

There is therefore provided, in accordance with an embodiment of the invention, a method for identifying a patient as being suitable for implantation of a weight-loss assist device, including:
determining a weight of the patient at first and second tires;
determining whether a level of weight loss of the patient from the first time to the second time exceeds a weight loss threshold; and
responsively to determining that the level of weight loss does exceed the weight loss threshold, implanting the weight-loss assist device.

In an embodiment, determining whether the level of weight loss exceeds the weight loss threshold includes identifying a weight loss reduction corresponding to an excess weight loss of at least 3% during a period lasting between 3 and 6 weeks.

There is further provided, in accordance with an embodiment of the invention, a method for identifying a patient as being suitable for implantation of a weight-loss assist device, including:
measuring a gastric emptying rate of the patient;
determining whether the gastric emptying rate exceeds a gastric emptying rate threshold; and
responsively to determining that the gastric emptying rate does exceed the gastric emptying rate threshold, implanting the weight-loss assist device.

In an embodiment, determining whether the gastric emptying rate exceeds the gastric emptying rate threshold includes identifying a gastric emptying rate corresponding to a level of gastric retention at two hours of less than 40%.

In an embodiment, determining whether the gastric emptying rate exceeds the gastric emptying rate threshold includes identifying a gastric emptying rate corresponding to a level of gastric retention at two hours of less than 30%.

In an embodiment, determining whether the gastric emptying rate exceeds the gastric emptying rate threshold includes identifying a gastric emptying rate corresponding to a gastric half-emptying time of less than 110 minutes.

In a embodiment, the method includes:
determining a weight of the patient at first and second times; and
determining whether a level of weight loss of the patient from the first time to the second time exceeds a weight loss threshold,
wherein implanting the weight-less assist device includes implanting the weight-loss assist device responsively to determining that the gastric emptying rate exceeds the gastric emptying rate threshold and responsively to determining that the level of weight loss exceeds the weight loss threshold.

There is still further provided, in accordance with an embodiment of the invention, a method for identifying a patient as being suitable for implantation of a weight-loss assist device, including:
identifying the patient as being generally suitable for the implantation;
subsequently, measuring a value associated with the patient; and
responsively to determining that the value is beyond a threshold associated therewith, implanting the weight-loss assist device.

In an embodiment, measuring the value includes measuring a rate of gastric emptying.

In an embodiment, identifying the patient as being generally suitable includes performing a physical examination and evaluating a medical history of the patient.

In an embodiment, measuring the value includes measuring a level of weight loss.

In an embodiment, measuring the level of weight loss includes placing the patient in diet counseling.

There is also provided, in accordance with an embodiment of the invention, a method for identifying a patient as being suitable for implantation of a weight-loss assist device, including:
identifying the patient as being generally suitable for the implantation;
subsequently, measuring a value associated with the patient; and
responsively to determining that the value is beyond a threshold associated therewith, implanting the weight-loss assist device.

There is additionally provided, in accordance with an embodiment of the invention a method for identifying a patient as being suitable for implantation of a weight-loss assist device, including:

determining a weight of the patient at first and second times;

determining whether a level of weight loss of the patient from the first time to the second time exceeds a weight loss threshold; and responsively to determining that the level of weight loss does exceed the weight loss threshold, implanting the weight-loss assist device.

There is still additionally provided, in accordance with an embodiment of the invention, a method for identifying a patient as being suitable for implantation of a weight-loss assist device, including:

measuring a gastric emptying rate of the patient; determining whether the gastric emptying rate exceeds a gastric emptying rate threshold; and responsively, to determining that the gastric emptying rate does exceed the gastric emptying rate threshold, implanting the weight-loss assist device.

There is yet additionally provided, in accordance with an embodiment of the invention, a method for identifying a patient as being suitable for implantation of a weight-loss assist device, including:

measuring a first rate of gastric activity of the patient, prior to food intake by the patient, measuring second rate of gastric activity of the patient, subsequently to the food intake;

comparing a difference between the first and second rates to a threshold; and in response to the comparing, implanting the weight-loss assist device.

In an embodiment, comparing includes determining whether the difference is above a threshold.

In an embodiment, comparing includes determining whether the difference is below a threshold.

In an embodiment, determining includes subtracting one of the rates from the other rate.

In an embodiment, determining includes calculating a ratio of the rates.

In an embodiment, determining includes setting the threshold to be greater than 40%.

In an embodiment, determining includes setting the threshold to be less than 40%.

In an embodiment, determining includes setting the threshold to be greater than 5%.

In an embodiment, determining includes setting the threshold to be between 5% and 40%.

In an embodiment, determining includes setting the threshold to be between, 15% and 25%.

In an embodiment, measuring the first and second rates of gastric activity includes measuring first and second rates of propagating slow waves, respectively.

In an embodiment, measuring the first and second rates includes measuring the rates non invasively.

In an embodiment, measuring, the first and second rates includes measuring the rates invasively.

In an embodiment, measuring the first and second rates includes temporarily coupling a measurement electrode to a gastric muscle of the patient.

There is also provided, in accordance with an embodiment of the invention, a method for identifying a patient as being suitable for implantation of a weight-loss assist device, including:

measuring a first rate of gastric activity of the patient; subsequently, applying electrical stimulation to the patient; subsequently, measuring a second rate of gastric activity of the patient; determining whether a difference between the first and second rates is above a threshold; and in response to determining that the difference is above the threshold, implanting the weight-loss assist device.

In an embodiment, measuring the first and second rates of gastric activity includes measuring first and second rates of propagating slow waves, respectively.

In an embodiment, measuring the first and second rates includes temporarily coupling a measurement electrode to a gastric muscle of the patient.

In an embodiment, applying electrical stimulation to the patient includes temporarily coupling a measurement electrode to a gastric muscle of the patient.

In an embodiment, determining includes subtracting one of the rates from the other rate.

In an embodiment, determining includes calculating a ratio of the rates.

In an embodiment, determining includes setting the threshold to be less than 20%.

In an embodiment, determining includes setting the threshold to be between 20% and 40%.

In an embodiment, determining includes setting the threshold to be greater than 40%.

The present invention will be more fully understood from the following detailed description of embodiments thereof, taken together with the drawings, in which:

BRIEF DESCRIPTION OF THE DRAWINGS

FIGS. 2 and 3 are graphs showing gastric emptying rate data for two sets of patients, acquired and analyzed in accordance with an embodiment of the present invention;

DETAILED DESCRIPTION OF EMBODIMENTS OF THE INVENTION

Figure 1:
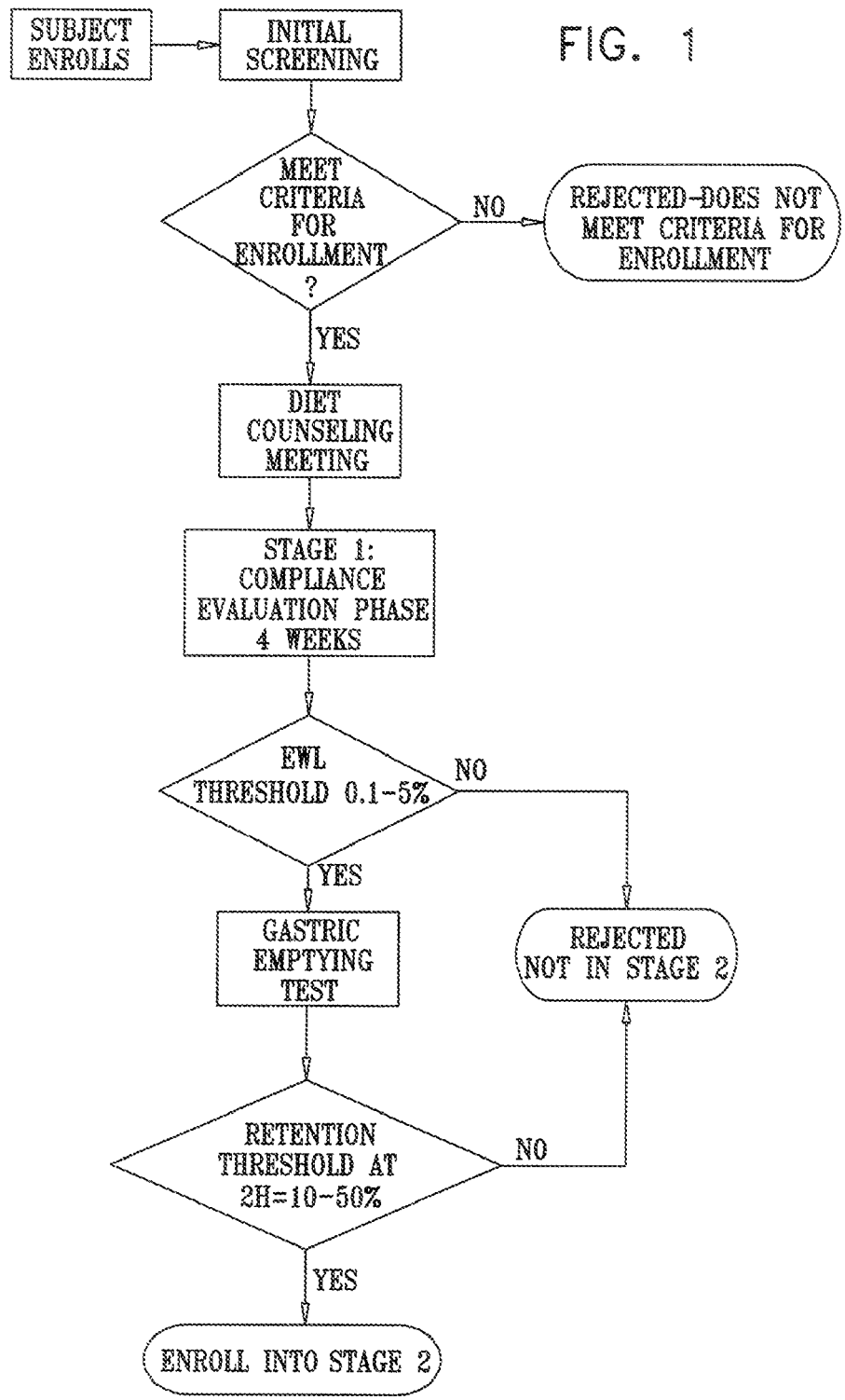
FIG. 1 is a flow chat showing a method for selecting patients, in accordance with an embodiment of the present invention.

FIG. 1 is a flow chart showing a method for identifying patients who are suitable to have a weight-loss assist device implanted, in accordance with an embodiment of the present invention, As is shown in the flow chart, a patient who wants to lose weight requests to enroll, and initial screening determines whether the patient is a generally-suitable candidate for implantation of the weight-loss assist device. For example, a generally-suitable candidate may be identified based on weight, height, age, and desire to undergo the implantation procedure. Unsuitable candidates are not permitted to enroll, but may be encouraged to seek other forms of treatments (e.g., ongoing diet and lifestyle counselling). Candidates who are identified as being generally suitable are enrolled in an evaluation program, in which one or more tests are performed in order determine whether the candidate is in: (a) a first population, which includes patients who are likely to benefit from the implantation of the device, or (b) a second population, which includes patients who are not likely to derive substantial benefit from the implantation.

In the first stage of the evaluation program, as show in FIG. 1, the patient is weighed, and counseled regarding changes in diet and/or lifestyle which are likely to help produce weight loss. At a later point (e.g., about 2-6 weeks or about 6-20 weeks following counselling or initiation of counselling), the patient's weight is measured again. An excess weight loss greater than a threshold between about 2% and about 3% (such as, for example, about 2%, 2,5%, 2.775%, or 3%) is used to determine that the patient is likely to benefit from implantation. In an embodiment, the, threshold is less than 2% (e.g., it is between 0.1% and 2%), or greater than 3% (e.g., it is between 3% and 5%). For some applications, the weight loss threshold is expressed as a rate of weight loss (e.g., a threshold of about 0.1-5% EWL/month, typically a threshold of 0.5-1.5% EWL/month).

Patients who do not lose at least the threshold amount of weight are typically rejected as candidates for implantation of the weight-less assist device. Alternatively, the lack of sufficient weight loss during the first stage of the evaluation program is used as an indicator against the implantation, but does not, in and of itself, result rejection of the patient as a candidate for implantation.

Subsequently, some or all of the patients undergo testing of gastric emptying rate. For some applications, techniques for measuring gastric emptying are utilized that are described in the above-referenced article by Tougas et al. and/or the above-referenced article by Choi et al., which are incorporated herein by reference. Typically, if the rate of gastric emptying is faster than a threshold, then the patient is determined to be likely to benefit from implantation of the device. For example, if the patient's gastric half-emptying time is less than about 80, 90, or 100 minutes, then the patient may be determined to be likely to benefit from implantation. Alternatively or additionally, if the level of gastric retention at two hours is less than about 20%, 30%, or 40% then the patient may be determined to be likely to benefit from implantation.

Typically, but not necessarily, the gastric emptying threshold rate is in a range which is considered to be a generally normal emptying rate for healthy people (e.g., 10-50% retention at two hours and/or t½ of 30-100 minutes). Thus, it may be that some patients with non-pathological gastric emptying rates are rejected as candidates for implantation of the weight-loss assist device.

It is noted that although FIG. 1 shows a requirement of both above-threshold weight loss and above-threshold gastric emptying rate in order to determine that a patient is a suitable candidate for implantation of the weight-loss assist device, the scope of the present invention includes performing only one of these tests, or combining the tests using a weighting function.

In addition to or instead of the tests for weight loss and gastric emptying rate described hereinabove the scope of the present invention includes identifying one or more of the following in order to facilitate an identification of a patient as a suitable candidate for having a weight-loss assist device implanted:

prolonged history of excess weight, such as from about 11-40 years, e.g., greater than 15, 18, or 20 years, type of obesity (e.g., peripheral), quality of if questionnaire scores, such as a RAND-36 test showing a pain factor score above 70, 75, or 80, scores on the three actor eating questionnaire (TFEQ) (e.g., cognitive control score range between 1 and 20, for example, less than about 9, or between about 4 and about 8 or 9), initial weight (e.g., range of 80-130 kg, or a range between about 100 and about 120 or 125 kg), and socioeconomic conditions (e.g., patients with greater motivation or social support structures to maintain lifelong weight control).

FIGS. 2 and 3 are graphs showing gastric emptying rate data for two sets of patients, acquired and analyzed in accordance with an embodiment of the present invention. In this study, a weight-loss assist device was implanted in 16 patients. (Data shown in FIGS. 2 and 3 represent results from 15 of the patients; gastric emptying rate data for the 16 the patient are missing due to a technical problem.).

The weight-loss assist device comprised a set of electrodes implantable on the funds, a set of electrodes implantable on the antrum, and a control unit. The control unit received data from the fundic electrodes indicative of stretching of the fundus, and data from the antral electrodes indicative of changes in the rate of slow wave propagation. The control unit analyzed the data from both sets of electrodes, and determined whether there was a high likelihood that a meal was being eaten. Upon such a determination, the control unit drove the antral electrodes to apply an ETC signal as a pulse train immediately following, detected gastric electrical activity. In general, a pulse train frequency of approximately 40-120 Hz is believed to be particularly suitable, and in this study the frequency was approximately 80 Hz. The duration of ETC pulse trains (or DC signals) is generally optimal if between approximately 500 and 2500 ms, and the duration of the ETC pulse trains in is study was typically approximately 1200 ms. Peak-to-Peak ETC signal amplitudes between approximately +/−6 mA and +/−16 mA, typically from +/−8 mA to +/−12 mA were applied. The applied signal tends to reduce eating in many patients.

In this study, measurements were taken regarding the rate of gastric emptying three weeks following implantation, but prior to initiating weight-loss treatment by applying a signal the stomach of each patient. A range of gastric emptying rates was identified, most of which being gastric half-emptying times from 60 to 120 minutes, and levels of retention at two hours from 15%/ to 45%. It is noted that this range of gastric emptying rates is generally considered normal.

The weight-loss assist device was activated six weeks after implantation. Patients' weights and overall health were monitored. At 20 weeks post-implantation, patients were divided into two groups based on weight loss compared to pre-implantation, weight. Patients whose excess weight loss was greater than 10% were assigned to group A. Patients whose EWL was less than 10% were assigned to group B.

The pre-activation gastric emptying rates of the patients in both groups were retrospectively analyzed, and these results are shown in FIGS. 2 and 3. It is seen that patients who lost more weight (group A) had significantly higher gastric emptying rates than those in group B, who lost less weight ($p<0.01$, t-test).

It is noted that the rates of gastric emptying for all patients in the study were within the normal range, and that patients in group B ("slow" gastric emptying rate patients) were all asymptomatic with respect to their gastric emptying rates.

Figure 4:
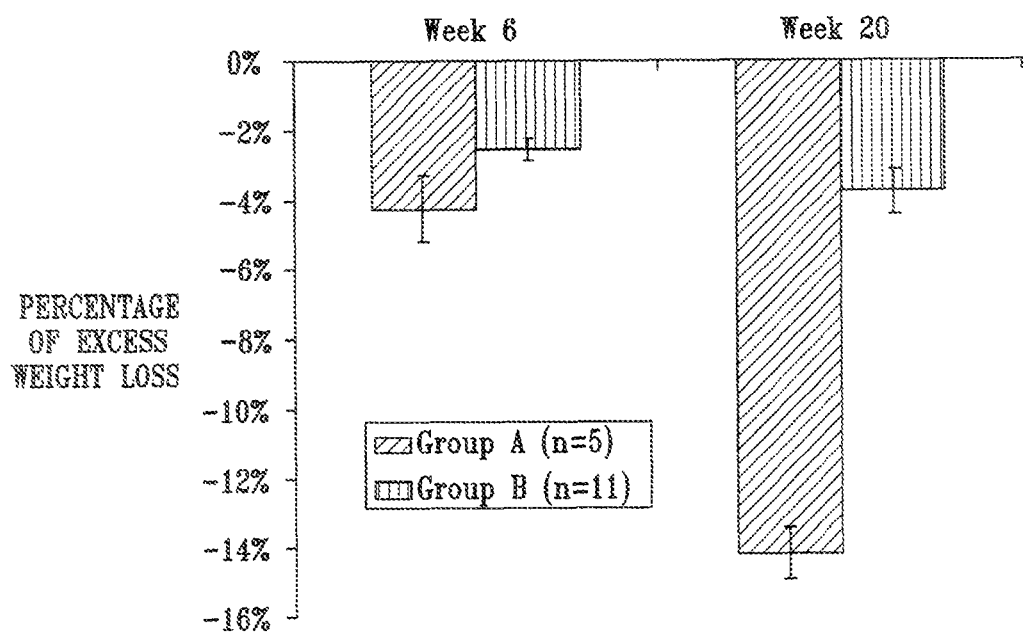
FIG. 4 is a graph showing weight loss data for two sets of patients, acquired and analyzed in accordance with an embodiment of the present invention.

FIG. 4 is a graph showing weight loss data for the 16 patients in groups A and B, acquired and analyzed in accordance with an embodiment of the present invention. Six weeks after implantation of the weight-loss assist device, but prior to activation of the device to initiate weight-loss treatment, the weight of each patient was measured, and these weight results are shown in FIG. 4. Patients in group A are seen to tend to have higher excess weight loss than patients in group B at week 6. Patients in group A had significantly greater excess weight loss than patients in group B after 14 weeks A therapy with the weight-loss assist device, i.e., at week 20 post-implantation (p <0.01). In other words, patients who eventually would lose more than 10% of their excess weight after 14 weeks of therapy could generally be identified retrospectively, based on their weight loss due to diet counselling.

Figure 5:
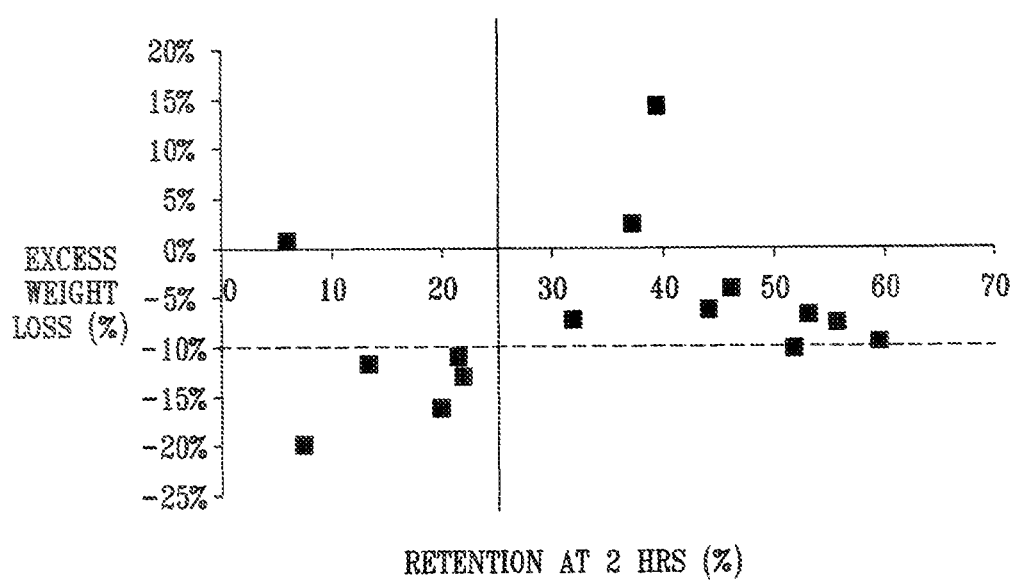
FIG. 5 is a graph showing excess weight loss in multiple patients as a function of gastric emptying rate, acquired and analyzed in accordance with an embodiment of the present invention.

FIG. 5 is a graph showing excess weight loss in the above-described 15 patients as a function of gastric emptying rate three weeks following implantation, but prior to initiating weight-loss treatment, acquired and analyzed in accordance with an embodiment of the present invention. (As noted above, gastric emptying rate data for the 16the patient are missing due to a technical problem.) It is seen that 5 out of 6 patients having less than 25% retention at 2 hours lost more than 10% of their excess weight after 14 weeks of therapy. Additionally, 8 out of 9 patients having more than 25% retention at 2 hours lost less than 10% of their excess weight after 14 weeks of therapy.

Figure 6:
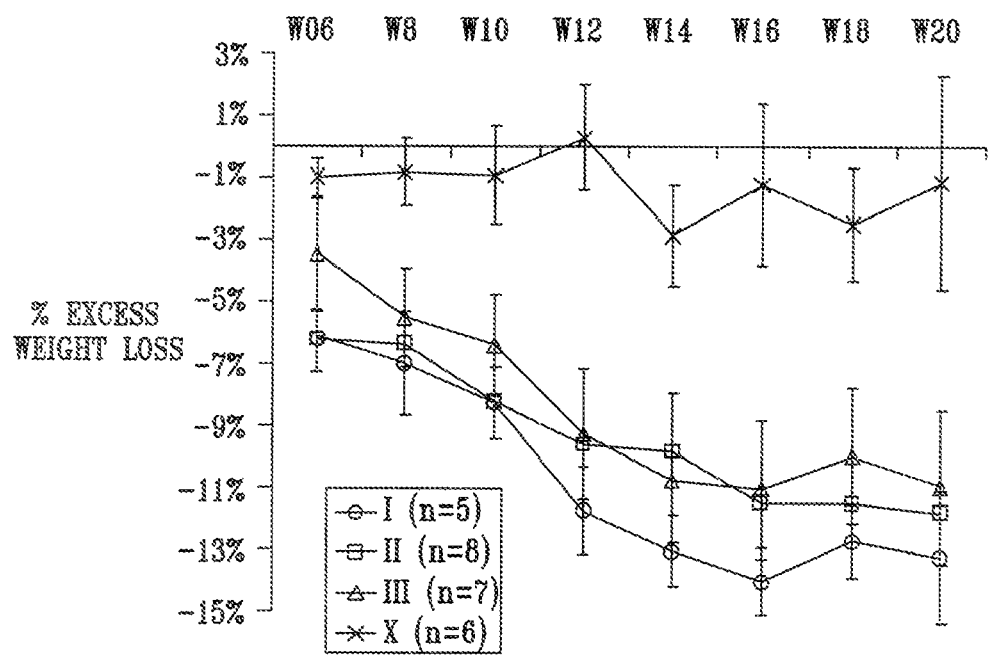
FIG. 6 is a graph showing weight loss curves for different patient populations, acquired and analyzed in accordance with an embodiment of the present invention.

FIG. 6 is a graph showing weight loss curves for different patient populations, acquired and analyzed in accordance with an embodiment of the present invention. In particular, FIG. 6 shows the percent excess weight loss that would have been achieved had the patients in this study been screened using one of the following screening procedures provided in accordance with some embodiments of the present invention:

Procedure I: Screen for (a) at week 6, EWL, greater than 3%, and (b) at week 3, meal retention at two hours less than 35%, Procedure II: Screen for EWL, at week 6 greater than 3%, and Procedure III: Screen at week 3 for meal retention at two hours less than 35%.

Procedure X: For comparison, weight loss for patients who would have been rejected according to Procedures I and II is shown in FIG. 6, as well.

Figure 7:
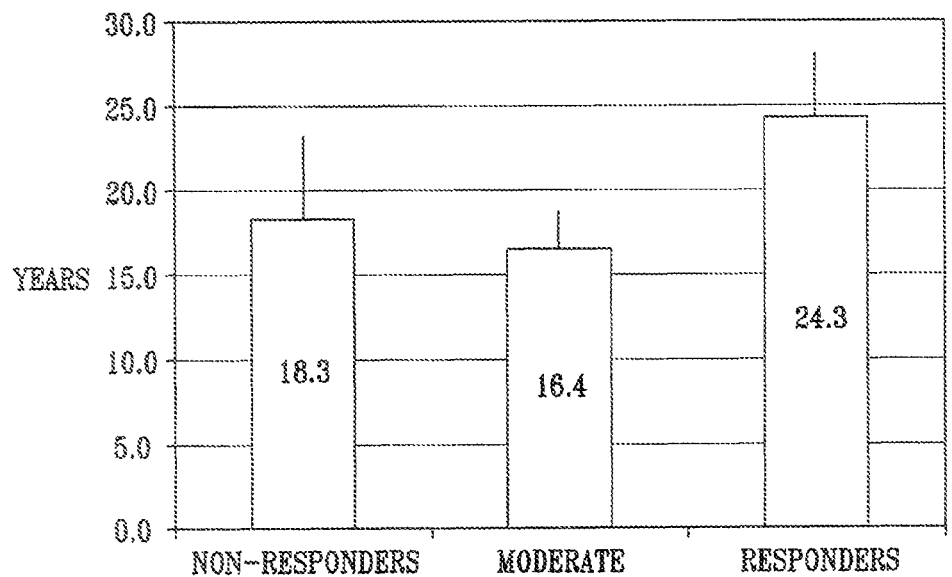
FIGS. 7-11 are additional graphs showing respective selection criteria and their relationship to the different patient populations, acquired and analyzed in accordance with respective embodiments of the present invention.
Figure 8:
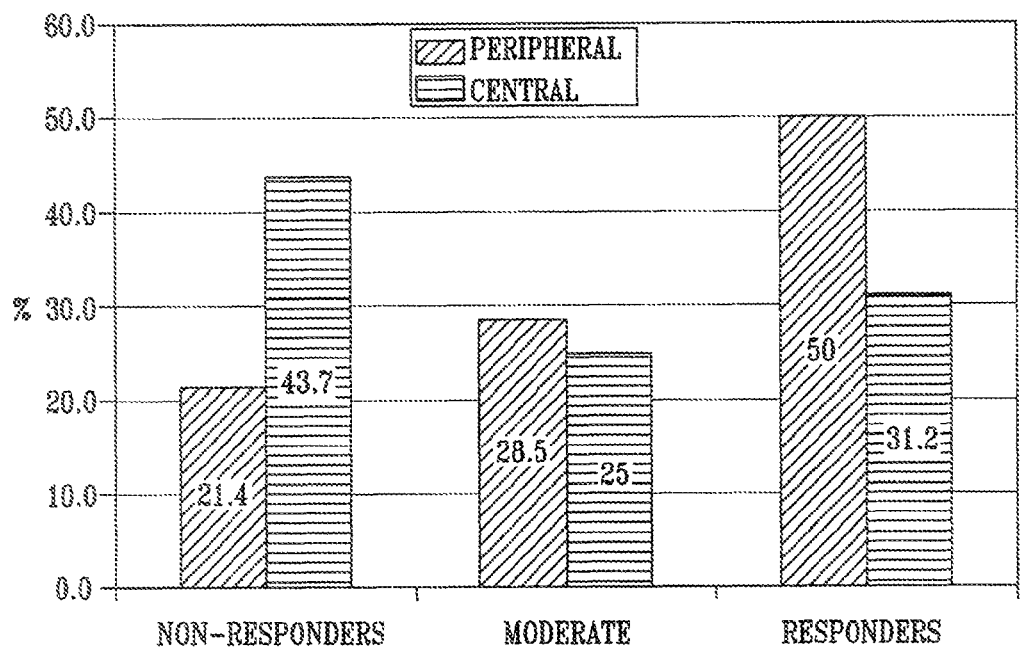
Figure 9:
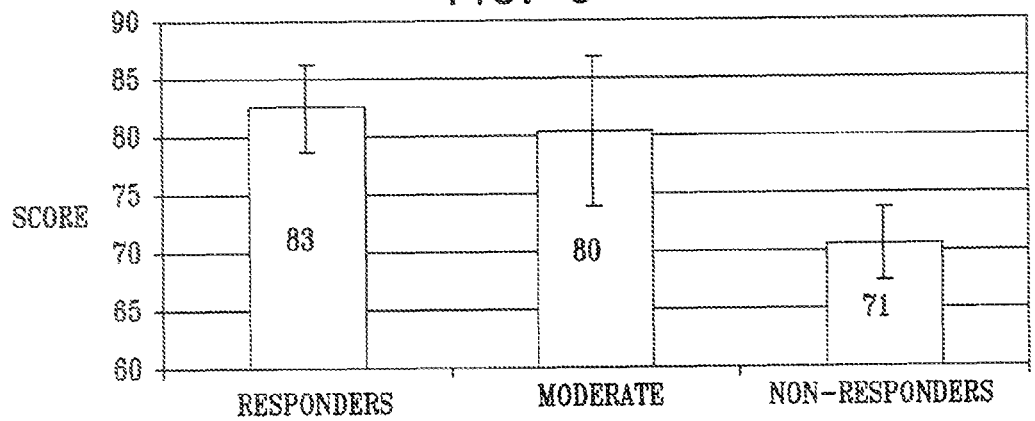
Figure 10:
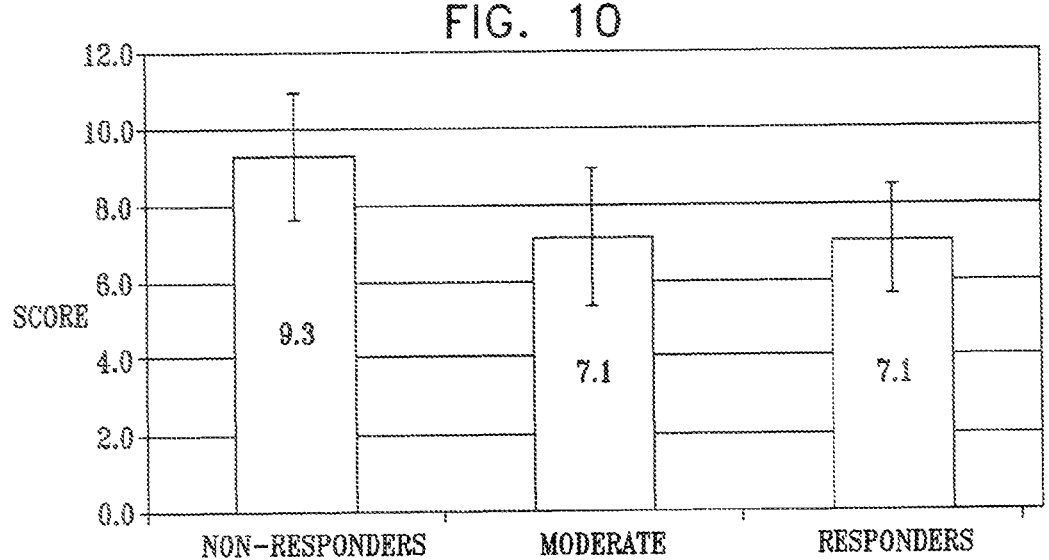
Figure 11:
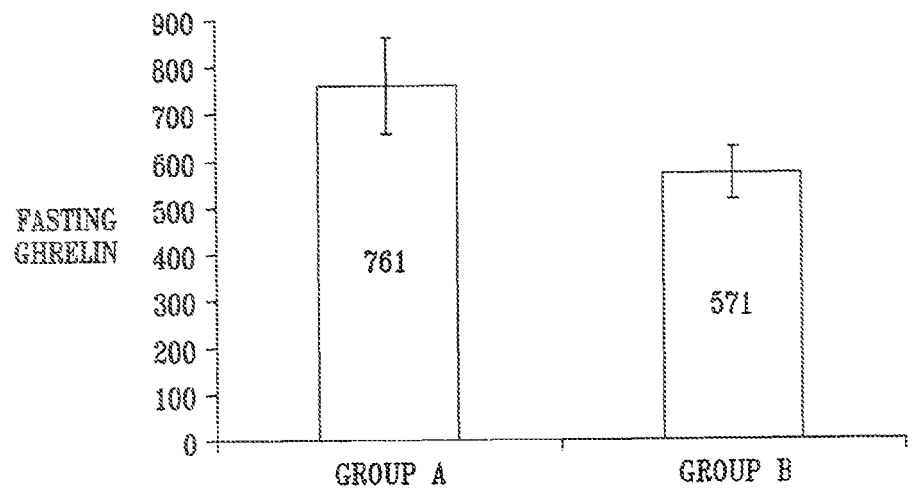

FIG. 7-11 are additional graphs showing respective selection criteria and their relationship to different patient populations, acquired and analyzed in accordance with respective embodiments of the present invention. The 16 patients described hereinabove are a subset of a group of 33 patients. The study on the additional 17 patients was initiated after that described hereinabove with respect to the 16 patients, FIGS. 7, 8, and 10 show results with respect to the group of 33 patients. FIGS. 9 and 11 are graphs showing data with respect to the 16 patients. (Tests described hereinbelow with reference to FIGS. 9 and 11 were only performed on the 16 patients.)

FIG. 7 is a graph showing the results of analyzing the group of 33 patients in whom the weight loss assist device described hereinabove was implanted. "Non-responders" (n=11) were classified as those with an EWL of less than 5% at 8 weeks after initiation of therapy. "Moderate responders" (n=5) were those with an EWL between 5% and 10%. "Responders" (in=17) were those with an EWL, greater than 10%.

It is seen that responders tended to have been overweight for a longer time than non-responders and moderate responders. In an embodiment of the present invention, a longer duration of a patient's excess weight is used as a positive indicator for implantation of a weight-loss assist device. For example, durations greater than 10, 15, 20, or 25 years may be used to indicate in favor of implantation. Alternatively or additionally, a weighted scale may be applied in the decision process, favoring implantation in accordance with increasing duration of a patient's excess weight.

FIG. 8 shows results for the same patient groups (responders, moderate responders, non-responders), with respect to the parameter of obesity type Of the 33 patients represented in FIG. 8, fifteen had peripheral obesity, and eighteen had central obesity. FIG. 8 shows a general tendency towards higher responsiveness to therapy by the weight-loss assist device in patients with peripheral obesity compared to patients with central obesity. For example, 50% of patients with peripheral obesity were found to be responders, while 31% patients with central obesity were found to be responders. Similarly, only 21% of patients with peripheral obesity were non-responders, while 44% of patients with central obesity were non-responders. In an embodiment of the present invention, a patient's peripheral obesity is a favorable indicator for implantation of a weight-loss assist device.

FIG. 9 shows results in the 16 patents, with respect to the parameter of the RAND-36 pain factor score. Responders tended to have a higher score (avg.=83) than non-responders (avg.=71). In an embodiment of the present invention a higher score on the RAND-36 test with respect to pain (or similar results on a similar test) is used as a favorable indicator for implantation of a weight-loss assist device. For example, a score greater than 70, 75, or 80, or a weighted analysis of the score, may be used as a favorable indicator for implantation.

It noted that some embodiments described herein relate to assessing patient pain and identifying the patient as being appropriate for implantation of a weight-loss assist device in response to a lower-than-threshold level of pain. For some applications, these embodiments are supplemented or replaced by an evaluation of another psychological and/or questionnaire-based factor, and identifying the patient as being appropriate for implantation of the device in response to an assessment that is "healthier" than a threshold. Thus, other scales of the SF-36 may be used, or another indicator of overall physical health, mental health, social acceptance, etc.

FIG. 10 shows results for the group of 33 patients, with respect to the parameter of cognitive control scale of the three factor eating questionnaire (TFEQ). Responders tended to have lower scores (avg.=7.1) than non-responders (avg.=9.3). In an embodiment, TFEQ cognitive control scores of less than about 9, or between about 4 and about 8 or 9, are used as indicators favoring implantation of a weight-loss assist device.

FIG. 11 is a graph comparing fasting ghrelin levels in patients from Group A(n=5) and Group B (n=11), described hereinabove. The patients in Group A, who had greater than 10% EWL, are seen to tend to have higher ghrelin levels (avg.=761 ng/ml) than patients in Group B (avg.=571 n/ml), p=0.09. In an embodiment, higher ghrelin levels (e.g., greater than 500, 550, 600, 650, or 700 ng/ml) are used as an indicator favoring implantation of a weight-loss assist device.

A variety of tests are described herein for determining the suitability of a patient for implantation of a weight-loss assist device. It is noted that the scope of the present invention includes performing only a single one of these tests, or combining two or more of the tests using a weighting function. For example, a combination score may be generated based on:

2-hour gastric retention (GR)–1 point for 20% <GR<30%, 2 points for 5% <GR<=20%;

(b) excess weight loss 3-6 weeks 4 weeks) after initiating counselling–1 point for 2% <EWL<3%, 2 points for 3% <=EWL<4%, 3 points EWL>4%;

(c) number of years of obesity–1 point for 15-20, 2 points for greater than 20;

(d) type of obesity–1 point for peripheral;

(e) RAND)-36 pain factor score (PF)–1 point for 70<PF<75, 2 points for 75<=PF<80, and 3 points for PF>=80;

(f) cognitive control scale of the TFEQ–1 point for 7<=TFEQ<=8, 2 points for TFEQ<7; and (g) fasting ghrelin levels (GL)–1 point for 600 ng/ml<GL<700 ng/ml, 2 points for GL>=700 ng/ml.

In an embodiment, patients with a combined score of at least 4 are accepted for implantation of a weight-loss assist device. In some embodiments of the invention, patients with a combined score of at least 6, 7, or 8 are accepted, while in other embodiments, patients with a combined score of at least 3 are accepted. It is to be understood that some elements of the combined score may be eliminated from the list and the scoring mechanism modified accordingly. Similarly, other elements may be added to the list and the scoring mechanism modified accordingly.

It is noted that although techniques described hereinabove relate to screening patients to determine whether they are suitable for implantation of a weight-loss assist device that provides electrical stimulation, the scope of the present invention includes using the techniques described herein for screening patients to determine their suitability for other invasive procedures, as well. For example, these techniques may be used to determine a patient's suitability for undergoing gastric banding or any other surgical procedure for treating obesity. Similarly, the scope of the present invention includes using, the screening techniques described hereinabove to identify patients who would be most likely to benefit from implantation of a diabetes-treatment device (e.g., that applies electrical stimulation to the pancreas or gastrointestinal tract), instead of or in addition to implantation of a weight-loss assist device.

For some applications, the screening procedures described hereinabove are used to screen patients prior to implantation of a device that employs techniques described in one or more of the following references, which are described in the Background of the present patent application and are incorporated herein by reference: U.S. Pat. No. 6,600,953 to Flesler et al., U.S. Pat. No. 6,571,127 and PCT Patent Publication WO 99/03533 to Ben-Haim. et al., and U.S. Patent Application Publication 2004/147816 to Policker et al.

It will be appreciated by persons skilled In the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
measuring a gastric emptying rate of the patient;
determining whether the gastric emptying rate exceeds a gastric emptying rate threshold in order to determine whether the patient is in (a) a first population who are likely to derive substantial benefit from implantation of an electrical stimulation treatment device or (b) a second population who are not likely to derive substantial benefit from the implantation; and
responsively to determining that the gastric emptying rate does exceed the gastric emptying rate threshold;
determining that the patient (a) is in the first population, and (b) is not in the second population;
implanting the electrical stimulation treatment device in the patient; and
activating the electrical stimulation treatment device to treat the patient by applying electrical stimulation to the patient,
wherein the substantial benefit includes at least one benefit, following activation of the electrical stimulation treatment device, selected from the group consisting of; at least a threshold amount of weight loss, and improved control of blood sugar.

2. The method according to claim 1, wherein determining whether the gastric emptying rate exceeds the gastric emptying rate threshold comprises identifying a gastric emptying, rate corresponding to a level of gastric retention at two hours of less than 40%.

3. The method according to claim 1, wherein determining whether the gastric emptying rate exceeds the gastric emptying rate threshold comprises identifying a gastric emptying rate corresponding to a level of gastric retention at two hours of less than 30%.

4. The method according to claim 1, wherein determining whether the gastric emptying rate exceeds the gastric emptying rate threshold comprises identifying a gastric emptying rate corresponding to a gastric half-emptying time of less than 110 minutes.

5. The method according to claim 1, comprising:
determining a weight of the patient at first and second times; and
determining whether a level of weight loss of the patient from the first time to the second time exceeds a weight loss threshold,
wherein implanting the electrical stimulation device comprises implanting the weight-loss assist device responsively to determining that the gastric emptying rate exceeds the gastric emptying rate threshold and responsively to determining that the level of weight loss exceeds the weight loss threshold.

6. A method comprising:
measuring a first rate of gastric activity of the patient, prior to food intake by the patient;
measuring a second rate of gastric activity of the patient, subsequently to the food intake;
comparing a difference between the first and second rates to a threshold in order to determine whether the patient is in (a) a first population who are likely to derive substantial benefit from implantation of an electrical stimulation treatment device or (b) a second population who are likely to derive substantial benefit from the implantation; and
in response to the comparing:
determining that the patient (a) is in the first population, and (b)is not in the second population;
implanting the electrical stimulation treatment device in the patient; and
activating the electrical stimulation treatment device to treat the patient by applying electrical stimulation to the patient,
wherein the substantial benefit includes at least one benefit, following activation of the electrical stimulation treatment device, selected from the group consisting of: at least a threshold amount of weight loss, and improved control of blood sugar.

7. The method according to claim 6, wherein comparing comprises determining whether the difference is above a threshold.

8. The method according to claim 6, wherein comparing comprises determining whether the difference is below a threshold.

9. The method according to claim 8, wherein determining comprises subtracting one of the rates from the other rate.

10. The method according t claim 8, wherein determining comprises calculating a ratio of the rates.

11. The method according to claim 8, wherein determining comprises setting the threshold to be greater than 40%.

12. The method according, to claim 8, wherein determining comprises setting; the threshold to be less than 40%.

13. The method according to claim 8, wherein determining comprises setting the threshold to be greater than 5%.

14. The method according to claim 8, wherein determining comprises setting the threshold to be between 5% and 40%.

15. The method according to claim 8, wherein determining comprises setting the threshold to be between 15% and 25%.

16. The method according to claim 8, wherein measuring the first and second rates of gastric activity comprises measuring first and second rates of propagating slow waves, respectively.

17. The method according to claim 8, wherein measuring the first and second rates comprises measuring the rates non-invasively.

18. The method according to claim 8, wherein measuring the first and second rates comprises measuring the rates invasively.

19. The method according, to claim 8, wherein measuring the first and second rates comprises temporarily coupling a measurement electrode to a gastric muscle of the patient.

20. A method comprising:
measuring a first rate of gastric activity of the patient;
subsequently, applying electrical stimulation to the patient;
subsequently, measuring a second rate of gastric activity of the patient;
determining whether a difference between the first and second rates is above a threshold in order to determine whether the patient is in (a) a first population who are likely to derive substantial benefit from implantation of an electrical stimulation treatment derive or (b) a second population who are not likely to derive substantial benefit from the implantation; and
in response to determining that the difference is the threshold:
  determining that the patient (a) is in the first population, and (b) is not in the second population;
  implanting the electrical stimulation treatment device in the patient; and
  activating the electrical stimulation treatment device to treat the patient by applying electrical stimulation to the patient,
wherein the substantial benefit includes at least one benefit, following activation of the electrical stimulation treatment device, selected from the group consisting of: at least a threshold amount of weight loss, and improved control of blood sugar.

21. The method according, to claim 20, wherein measuring the first and second rates of gastric activity comprises measuring first and second rates of propagating slow waves, respectively.

22. The method according to claim 20, wherein measuring the first and second rates comprises temporarily coupling a measurement electrode to a gastric muscle of the patient.

23. The method according to claim 20, wherein applying electrical stimulation to the patient comprises temporarily coupling a measurement electrode to a gastric muscle of the patient.

24. The method according to claim 20, wherein determining comprises subtracting one of the rates from other rate.

25. The method according to claim 20, wherein determining comprises calculating a ratio of the rates.

26. The method according to claim 20, wherein determining comprises setting the threshold to be less than 20%.

27. The method according to claim 20, wherein determining comprises setting the threshold to be between 20% and 40%.

28. The method according to claim 20, wherein determining comprises setting the threshold to be greater than 40%.

29. The method according to claim 1, wherein measuring the gastric emptying rate comprised providing a test meal for consumption by the patient.

30. The method according to claim 1, wherein the electrical stimulation treatment device is a weight-loss assist device, and wherein implanting the electrical stimulation treatment device comprises implanting the weight-loss assist device.

31. The method according to claim 1, wherein the electrical stimulation treatment device is a diabetes-treatment device, and wherein implanting the electrical stimulation treatment device comprises implanting the diabetes-treatment device.

32. The method according to claim 6, wherein the electrical stimulation treatment device is a weight-loss assist device, and wherein implanting the electrical stimulation treatment device comprises implanting the weight-loss assist device.

33. The method according to claim 6, wherein the electrical stimulation treatment device is a diabetes-treatment device, and wherein implanting the electrical stimulation treatment device comprises implanting the diabetes-treatment device.

34. The method according to claim 20, wherein the electrical stimulation treatment device is a weight-loss assist device, and wherein implanting the electrical stimulation treatment device comprises implanting the weight-loss assist device.

35. The method according to claim 20, wherein the electrical stimulation treatment device is a diabetes-treatment device, and wherein implanting the electrical stimulation treatment device comprises implanting the diabetes-treatment device.

* * * * *

UNITED STATES PATENT AND TRADEMARK OFFICE
CERTIFICATE OF CORRECTION

PATENT NO. : 8,442,841 B2  Page 1 of 1
APPLICATION NO. : 11/551282
DATED : May 14, 2013
INVENTOR(S) : Walid Haddad, Shai Policker and Keren Afek It is certified that error appears in the above-identified patent and that said Letters Patent is hereby corrected as shown below:

In the Claims:

Column 11, line 54, Claim 1, line 2, "the" should read -- a --.
Column 11, line 63, Claim 1, line 11, "threshold;" should read -- threshold: --.
Column 12, line 6, Claim 1, line 21, "of;" should read -- of: --.
Column 12, line 11, Claim 2, line 3, "emptying," should read -- emptying --.
Column 12, line 38, Claim 6, line 2, "the" should read -- a --.
Column 12, line 47, Claim 6, line 11, "are" should read -- are not --.
Column 13, line 3, Claim 10, line 1, "t" should read -- to --.
Column 13, line 7, Claim 12, line 1, "according," should read -- according --.
Column 13, line 8, Claim 12, line 2, "setting:" should read -- setting --.
Column 13, line 25, Claim 19, line 1, "according," should read -- according --.
Column 13, line 29, Claim 20, line 2, "the" should read -- a --.
Column 13, line 37, Claim 20, line 10, "derive" should read -- device --.
Column 13, line 40, Claim 20, line 13, "is" should read -- is above --.
Column 14, line 1, Claim 21, line 1, "according," should read -- accoding --.
Column 14, line 13, Claim 24, line 2, "from" should read -- from the --.
Column 14, line 24, Claim 29, line 2, "comprised" should read -- comprises --.

Signed and Sealed this
Seventeenth Day of September, 2013

Teresa Stanek Rea
*Deputy Director of the United States Patent and Trademark Office*